US010758317B2

(12) United States Patent
Yuan et al.

(10) Patent No.: US 10,758,317 B2
(45) Date of Patent: Sep. 1, 2020

(54) METHOD AND APPARATUS FOR TOOTH BODY AUTOMATIC PREPARATION BY DIGITAL CONTROLLED LASER LIGHT AND TOOTH RETAINER

(71) Applicant: Peking University School of Stomatology, Beijing (CN)

(72) Inventors: Fusong Yuan, Beijing (CN); Peijun Lv, Beijing (CN)

(73) Assignee: Peking University School of Stomatology, Beijing (CN)

( * ) Notice: Subject to any disclaimer, the term of this patent is extended or adjusted under 35 U.S.C. 154(b) by 0 days.

(21) Appl. No.: 16/677,642

(22) Filed: Nov. 7, 2019

(65) Prior Publication Data

US 2020/0085532 A1 Mar. 19, 2020

Related U.S. Application Data

(63) Continuation of application No. 15/028,374, filed as application No. PCT/CN2014/082825 on Jul. 23, 2014, now Pat. No. 10,500,017.

(30) Foreign Application Priority Data

Oct. 9, 2013 (CN) .......................... 2013 1 046703 8
Dec. 11, 2013 (CN) .......................... 2013 1 0671482

(51) Int. Cl.
*A61C 17/08* (2006.01)
*A61B 6/14* (2006.01)
(Continued)

(52) U.S. Cl.
CPC ............ *A61C 1/0046* (2013.01); *A61B 6/032* (2013.01); *A61B 6/14* (2013.01); *A61B 6/4085* (2013.01);
(Continued)

(58) Field of Classification Search
CPC ....... A61C 1/0046; A61C 1/082; A61C 17/08; A61C 9/0053; A61B 2034/105; A61B 2018/20359; A61B 2018/00636
(Continued)

(56) References Cited

U.S. PATENT DOCUMENTS 9,048,632 B1 * 6/2015 Dantus ................. H01S 3/2308
2008/0251720 A1 * 10/2008 Xu ........................ G01B 11/24
250/332

(Continued)

FOREIGN PATENT DOCUMENTS

CN 1182573 A 5/1998
CN 102715956 A 10/2012
CN 103327926 A 9/2013

*Primary Examiner* — Heidi M Eide
*Assistant Examiner* — Drew S Folgmann
(74) *Attorney, Agent, or Firm* — IPro, PLLC

(57) ABSTRACT

A digital control laser automatic tooth preparation method and device and a tooth positioner are provided. The device includes an intra-oral three-dimensional scanner, a dental laser, an oral working end of a digital control laser tooth preparation control system, an oral and maxillofacial cone beam CT scanner, a computer, a tooth positioner, a negative-pressure suction device and a real-time monitoring device. The computer is connected respectively with the intra-oral three-dimensional scanner, the dental laser, the oral working end of the digital control laser tooth preparation control system, the oral and maxillofacial cone beam CT scanner, the negative-pressure suction device, and the real-time monitoring device. The dental laser is connected with the oral working end of the digital control laser tooth preparation control system through a light guiding arm (1). The oral working end of the digital control laser tooth preparation control system is connected with the tooth positioner and the real-time monitoring device. The negative-pressure suction device is connected with the tooth positioner. The digital control laser automatic tooth preparation method and device according to embodiments of the present invention can replace part of manual operations of a doctor, uses a laser to replace a conventional mechanical grinding instrument, and can effectively improve the standard level and efficiency of clinical oral tooth preparation.

3 Claims, 5 Drawing Sheets

(51) Int. Cl.
  *A61C 1/00* (2006.01)
  *A61C 9/00* (2006.01)
  *A61C 1/08* (2006.01)
  *A61B 6/03* (2006.01)
  *A61B 6/00* (2006.01)
  *A61B 18/20* (2006.01)
  *A61B 34/10* (2016.01)
  *A61B 18/00* (2006.01)

(52) U.S. Cl.
  CPC .......... *A61B 6/5247* (2013.01); *A61C 1/0015* (2013.01); *A61C 1/082* (2013.01); *A61C 9/0053* (2013.01); *A61C 17/08* (2019.05); *A61B 2018/00636* (2013.01); *A61B 2018/20359* (2017.05); *A61B 2034/105* (2016.02)

(58) Field of Classification Search
  USPC .................................................. 606/13–19
  See application file for complete search history.

(56) References Cited

U.S. PATENT DOCUMENTS

| | | | |
|---|---|---|---|
| 2013/0059264 A1* | 3/2013 | Monty | A61C 1/0046 433/29 |
| 2014/0248577 A1* | 9/2014 | Tahmasebi | A61C 1/082 433/75 |
| 2015/0025855 A1* | 1/2015 | Fisker | A61C 8/0077 703/1 |
| 2015/0057675 A1* | 2/2015 | Akeel | G16H 50/50 606/130 |
| 2015/0164335 A1* | 6/2015 | Van Der Poel | A61B 5/0071 433/29 |

* cited by examiner

METHOD AND APPARATUS FOR TOOTH BODY AUTOMATIC PREPARATION BY DIGITAL CONTROLLED LASER LIGHT AND TOOTH RETAINER

This application claims priorities of Chinese patent application No. CN201310467038.5 filed to the State Intellectual Property Office of P.R.China on Oct. 9, 2013 and entitled "Digital control Laser Automatic Tooth Preparation Method and Device" and the Chinese patent application No. CN201310671482.9 filed to the State Intellectual Property Office of P.R.China on Dec. 11, 2013 and entitled "Miniature Automatic Dental-Preparation Cutting Device In Oral Cavity", the entire contents of which are hereby incorporated by reference.

FIELD OF THE INVENTION

The present invention relates to a tooth preparation technique, and particularly relates to a digital control laser automatic tooth preparation method and device, and a tooth positioner or retainer.

BACKGROUND OF THE INVENTION

1. Current Domestic and Aboard Clinical Applied Manual Tooth Preparation Technique.

In a conventional manual tooth preparation mode, it is difficult to meet standard requirements described in textbooks and clinical practices. The general level of manual tooth preparation in China is low (according to statistics from related experts, the qualified rate is about 40%). There is a lack of high-level dental doctors in China. Meanwhile, it often takes many years to cultivate a high-level clinician. These factors mentioned above together cause problems of "difficulties and high costs for accessing dental treatments". Furthermore, there is thus an urgent need to research and develop a brand-new automatic and intelligent clinical tooth preparation technique to replace the conventional manual mode.

2. Laser Cutting Technique for Tooth Hard Tissues

Some commercial Er:YAG and Er:YSGG lasers have been used for simple handheld laser-type tooth preparation such as removal of dental caries and dental cavity preparation, but the tooth surface after being cut by Er lasers is uneven and coarse, probably accompanying with generation of microcracks, and thus cannot meet the high precision requirement of oral cavity reparation and tooth preparation. Laser cutting of tooth hard tissues is characterized by high precision, concentrated action, small thermal damage and the like, can perform cutting under very low energy density and has cutting thresholds of 0.6-2.2 $J/cm^2$ and 0.3-1.4 $J/cm^2$ respectively for dental enamel and dentin, so it is expected to be a digital control tooth preparation tool with high precision. However, it has been reported in literatures that the laser cutting rates with respect to dental enamel and dentin are respectively $(0.05-3.6) \times 10^{-3}$ $mm^3/s$ and $(0.12-1.90) \times 10^{-3}$ $mm^3/s$, which are lower than those of a high-speed dental turbine handpiece (about 1 $mm^3/s$). Meanwhile, different from a conventional mechanical grinding head, the laser has no force feedback in the operating process, which is unfavorable for an operator to sense the position, direction and gesture and the like of the cutting tool and thus is also unfavorable for controlling the precision of the cutting path.

3. Automatic Control Technique Related to Laser Optical Path in a Narrow Space

Currently, some digital control laser-scanning optical path control techniques have already appeared abroad. As an example, the three-dimensional laser processing software TbPs400 matched with the three-dimensional laser processing equipment from TRUMPF group (a large-scale laser equipment manufacturer, German) is only effective for cutting circular tubes and rectangular tubes, and strictly speaking, is a 2.5-dimensional laser process. Moreover, the three-dimensional laser processing software FORMA provided by PRIMAINUSTRIE S.P.A (a famous laser equipment manufacturing enterprise, Italy) can only be used on such working stations as IBMRISC System16000. The PEPS Pentacut 3D cutting system provided by CAMTEK Limited (UK) has a huge competitive advantage since it not only reduces the construction period but also provides higher precision, but such software is very expensive and thus cannot be widely spread in the market. By investigation of the more than 20 laser equipment manufacturers (including Han's Laser, Wuhan Farley Laserlab Cutting system Engineering Co., Ltd, Shanghai Tuanjie Baichao CNC Laser Co., Ltd, Shanghai Unity Prima Laser Machinery Co., Ltd, and other domestic famous laser equipment manufacturers) taking part in the $11^{th}$ China internal machine tool exhibition (CIMT2009) held at April, 2009 in Beijing, it was found that the cutting machine tools exhibited by these exhibitors were substantially two-dimensional laser cutting machine tools, and only the Shanghai Unity Prima Laser Machinery Co., Ltd exhibited a three-dimensional laser cutting machine tool with the model number of SESAM02545, but the three-dimensional laser cutting automatic programming software matched with the same was the PEPS PentaCut developed by Camtek (UK). It demonstrates that currently domestic research of three-dimensional laser cutting equipment, particularly of an automatic programming system is still not sufficiently mature, which restricts the promotion of the three-dimensional laser cutting technique.

No related reports show that automatic control of a laser optical path has been realized for tooth preparation in a narrow space such as the oral cavity.

SUMMARY OF THE INVENTION

An object of the embodiments of the present invention is to provide a digital control laser automatic tooth preparation method which can replace part of manual operations of a doctor, wherein a laser is used to replace a conventional mechanical grinding instrument, thus can effectively improve the technical level of clinical treatment operations of a primary physician within a short time and improve the efficiency and quality of diagnosis and treatment. An object of the present invention is to provide a digital control laser automatic tooth preparation apparatus.

According to an aspect of the present invention, a digital control laser automatic tooth preparation method is provided, including the following steps:

1) acquiring three-dimensional surface scanning data of a crown portion of a target tooth with an intra-oral three-dimensional scanner, acquiring three-dimensional volume data of the crown portion of the target tooth with an oral and maxillofacial cone beam CT scanner, and storing the two sets of data respectively for subsequent reading operation;

2) registering the two sets of data with tooth preparation CAD software and unifying the data in the same coordinate system, and on a computer screen extracting edges of a tooth preparation, defining design parameters of the tooth preparation, and separating a dental enamel model portion, a dentin model portion and a dental pulp cavity model portion, so as to complete virtual modeling of the tooth preparation and obtain data of a virtual tooth preparation model, thereby finally storing the results as data of STL format;

3) automatically generating parameters related to a cutting process during the tooth preparation with laser tooth preparation CAM software according to the data of the virtual tooth preparation model acquired in step 2), and outputting the parameters into a digital control laser tooth preparation control system, wherein the parameters related to the cutting process include a focal spot diameter, a spot motion path and a scanning speed of the laser during tooth preparation;

4) fixing a tooth positioner onto a target tooth and meiso-distal adjacent teeth with a silicon rubber, removing the silicon rubber around the crown portion of the target tooth, acquiring integrated three-dimensional data of the tooth positioner and the target tooth with the intra-oral three-dimensional scanner again, registering the data of the virtual preparation model with the integrated three-dimensional data by using the tooth preparation CAD software, and rigidly connecting an intra-oral working end of the digital control laser tooth preparation control system to an occlusal opening end of the tooth positioner through a positioning post located on the tooth positioner, such that the spatial location relationship between the crown portion of the target tooth, the tooth positioner and the intra-oral working end of the digital control laser tooth preparation control system is unified and fixed;

5) in a coordinate system formed in step 4), completing accurate focusing of the laser at an initial position of the target tooth by using the laser tooth preparation CAM software, controlling a laser spot to automatically complete the tooth preparation process according to the scanning path and the scanning speed as set in step 3), and meanwhile in the process removing dental debris in real time by using a negative-pressure suction device mounted on the tooth positioner; and 6) after completing the tooth preparation, removing the intra-oral working end of the digital control laser tooth preparation control system and the tooth positioner from the oral cavity of a patient sequentially.

The tooth preparation CAD software includes a data reading module, a preprocessing module, a data fusion module, a constraint modeling module, and a postprocessing module.

Wherein:

The data reading module is configured to perform the following operations:

1) Reconstruction of CT data: reading the three-dimensional data reconstructed from a CT image into the tooth preparation CAD software, and performing lighting and rendering; and 2) Reconstruction of scanning data: reading three-dimensional surface scanning data acquired by scanning the target tooth and three-dimensional volume data acquired by the CT scanner into the tooth preparation CAD software and storing the same for facilitating subsequent reading operations.

The preprocessing module is configured to perform the following operations:

1) acquisition of curved surface of fusion region: firstly dividing the three-dimensional surface scanning data model M of the target tooth into a fusion region and a non-fusion region of which the point set is fixed, and clipping and extracting a fusion curved surface from the three-dimensional surface scanning data model M by using a finish line extraction algorithm based on a heuristic searching strategy;

2) Initial registration based on man-machine interaction: picking up three or more corresponding feature points from the three-dimensional volume data model N acquired by the CT scanner and the three-dimensional surface scanning data model M acquired by the intra-oral three-dimensional scanner, achieving alignment of the models through alignment of the feature points, calibrating feature points $s_i$ and $s_i'$ respectively on the three-dimensional volume data model N acquired by the CT scanner and the three-dimensional surface scanning data model M acquired by the intra-oral three-dimensional scanner, calculating a geometric transform matrix R, T between the feature points through $s_i'=s_iR+T$, and applying the matrix to the three-dimensional volume data model N acquired by the CT scanner and the three-dimensional surface scanning data model M acquired by the intra-oral three-dimensional scanner to perform an initial transformation, wherein this method can significantly reduce a translation error and a rotation error of model registration between subsequent iterative closest points (ICPs), and thus provides a good initial value for accurate registration; and 3) accurate registration based on ICP algorithm: after the initial registration, performing accurate registration by adopting an ICP algorithm, wherein the position registration between models is rotating and translating the coordinate system of the three-dimensional surface scanning data model M acquired by the intra-oral three-dimensional scanner and the coordinate system of the three-dimensional volume data model N acquired by the CT scanner in such a manner that the distance between homologous points is minimum, and making the least square between the spatial changed CT model N and the scanning model M approximate a target function by calculating the optimal rotation matrix $R^k$ and translation vector $T^k$ of the $k^{th}$ iteration, such that the f(R,T) reaches the minimum, as shown in equation (1):

$$f(R, T) = \frac{1}{N}\sum_{i=1}^{N} \|v_i' - (Rv_i + T)\|^2 \to \min \qquad (1)$$

wherein, P is the number of the feature points.

The data fusion module is configured to perform the following operations:

1) establishment of differential coordinate: introducing a Laplace operator coefficient matrix L, so as to ensure that the transformation between Cartesian coordinates and differential coordinates is performed in a matrix multiplication manner, as shown in equation (2) below:

$$\Delta = LV, L = I - D^{-1}A \qquad (2)$$

wherein $\Delta = \{\delta_i\}$ is a mesh differential coordinate, D is a diagonal matrix, $D_{ii} = d_i$, and A is an adjacency matrix of the mesh;

2) establishment of constraint condition: after the registration between the deformable curved surface of the three-dimensional volume data model N acquired by the CT scanner and the fixed curved surface of the three-dimensional surface scanning data model M acquired by scanning with the intra-oral three-dimensional scanner, realizing extraction of salient-featured points from the three-dimensional surface scanning data model M through a method which combines the mesh saliency and the Morse theory, wherein the constraint condition is in the deformable curved surface of the three-dimensional volume data model N searching closest points corresponding to the feature points extracted from the fixed curved surface of the three-dimensional surface scanning data model M;

3) iteration processing of deformation blending:

as a single deformation is liable to cause shape distortion of the mesh during the deformation from the deformable mesh of the three-dimensional volume data model N to the fixed mesh of the three-dimensional surface scanning data model M, employing a multi-iteration deformation strategy, i.e., dividing the single deformation into multi-step deformation, wherein this iteration strategy not only enables the deformed mesh to be naturally smooth but also avoids a mesh self-intersection phenomenon, the deformation amount b per time for example may be calculated according to equation (3) below, wherein n is the total number of iteration times, and k is the current number of iteration times:

$$b = \frac{1}{n-k}, k = 0, 1 \ldots n-1 \tag{3}$$

4) design of deformation weight coefficient: quantifying and assessing the degree of closeness between a deformable point and a target point by designing a weight matrix, wherein the weight matrix may be for example defined by equation (4) below:

$$w_i = w_d(k,d) \times w_a(\alpha) \tag{4}$$

wherein, $w_d(k,d)$ is a distance weighting function, k is the current number of iteration times, i is an index of a feature point, d is a distance between the current deforming point $g_i$ and a target deformation point $v_i$, $w_a(\alpha)$ is an angle weighting function, and $\alpha$ is an included angle between a normal direction of the deforming point $g_i$ and a ray direction $l_i$ from the gravity point of the three-dimensional surface scanning data model M to the deforming point; and 5) reconstruction of model mesh: introducing the aforementioned weight matrix W into a linear equation $$E(V') = \|L'V' - \delta\|^2 + \sum_{j \in C} \|v'_j - c_j\|^2$$

and an energy function $$\begin{pmatrix} L \\ I_{m \times m} \end{pmatrix} V' = L'V' = \begin{pmatrix} \delta \\ C \end{pmatrix},$$

so as to obtain equations (5) and (6), wherein L is a Laplacian matrix before the target mesh is deformed, I is an m-order unit matrix, L' is a Laplacian matrix after the target mesh is deformed, V' are the vertices after the target mesh is deformed, δ is a Laplacian coordinate of the target mesh, C is the deformation amount of the vertex, $v'_j$ is a coordinate after the deformation of a constraint vertex j, and $c_j$ is a deformation amount of the constraint vertex j;

$$E(V') = \|L'V' - \delta\|^2 + \sum_{j \in C} w\|v'_j - c_j\|^2 \tag{5}$$

$$\begin{pmatrix} L \\ wI_{m \times m} \end{pmatrix} V' = L'V' = \begin{pmatrix} \delta \\ wC \end{pmatrix} \tag{6}$$

when the energy function (6) takes the minimum value, in order to make the deformable mesh reach an expected deformation position, precomputation based on Cholesky decomposition is adopted during the solution of the minimum value so as to accelerate the solution, with the solutions respectively being x',y',z';

the constraint modeling module is configured to perform the following operations:

1) extraction of spatial-point-cloud data axes: extracting a dental long axis of a tooth by using an optimum spatial linear fitting method, wherein a directional vector in a space is S=(m,n,p) and a linear equation passing through a point $(x_0,y_0,z_0)$ is as shown in equation (7) below:

$$\frac{x - x_0}{m} = \frac{y - y_0}{n} = \frac{z - z_0}{y} \tag{7}$$

wherein $x_0,y_0,z_0$ is a three-dimensional coordinate value passing through any point, and m,n,p is a coordinate representation of the directional vector, an error equation as shown in equation (8) below is obtained according to a best square approximation theory:

$$f(\varepsilon_{i1}, \varepsilon_{i2}, \varepsilon_{i3}) = \Sigma_{i=0}^{q} (\varepsilon_{i1}^2, \varepsilon_{i2}^2, \varepsilon_{i3}^2) \tag{8}$$

wherein $\varepsilon_{i1}$, $\varepsilon_{i2}$, $\varepsilon_{i3}$ are respectively error components of the $i^{th}$ point in the point cloud in directions of the X axis, the Y axis and the Z axis of the fitting straight line, and q is the number of the points;

this non-linear ternary quadratic equation is solved by using an optimum gradient method to obtain an optimum directional vector (m,n,p), and this directional vector can be used together with known midpoints to solve a straight line, i.e., the axis of the tooth;

2) spatial curve projection: discretizing a finish line into data point sets by using a dense line projection method, projecting the points onto the three-dimensional volume data model acquired by the CT scanner along a curvature direction point by point, and connecting respective projected points to obtain a projection curve;

3) bias of discrete model: biasing the model by using a point-based bias algorithm, wherein multiple vectors on the vertices of the mesh are classified depending on types and are endowed with different weight values, and the calculation equation of the bias direction is as shown in equation (9) below:

$$\vec{V}_{Offset} = \sum_{j=1}^{n} W_j \cdot \vec{N}_{i,j} \tag{9}$$

wherein $V_{offset}$ is the bias direction of a point, 1 . . . n is the number of triangular patches surrounding the vertex in a circle, $W_j$ is a weight value varying with the type of the triangular patch, $N_{ij}$ is a normal vector corresponding to respective triangular patches surrounding the vertex in a circle, and the biased model is obtained by biasing respective points in the normal vector direction of each point;

4) analysis and solution of model constraint equation set: setting up a model constraint equation set (10) by analyzing dimensional chain relationships of a constraint model:

$$\begin{cases} \frac{L}{2} = L_1 + L_x + L_3 \\ H = L_2 + L_y + L_4 \\ \tan \alpha = \frac{L_x}{L_y} \end{cases} \tag{10}$$

wherein, L represents a total buccolingual length; H represents a total longitudinal height of a certain section; $l_1$ and $l_3$ respectively represent a shoulder width and a distance from a surface edge to a long axis of the tooth; $h_1$ and $h_3$ respectively represent a surface preparation thickness and a distance from the finish line to a certain lower designated location; α is the axial wall inclination of the preparation; and $l_2$ and $h_2$ are respectively an edge length and a height corresponding to α, for a complete preparation, n=3 and m=2, wherein $L_1$, $L_2$ and α are three parameterized variable values; for a designated tooth, H, L and $L_4$ are fixed values, and when the parameter values are given, the equation set is the one containing three unknowns, such that a set of values of $L_x$, $L_y$ and $L_3$ can be determined uniquely from the three known equations so as to uniquely determine a preparation model, and thus the spatial positions of respective portions of the model can be determined by solving this constraint equation; and 5) parametric modeling of multi-constraint model: driving modeling of a preparation through a parametric operation method, and realizing parametric and dynamic modifications of the model through a history-based method;

the postprocessing module is configured to perform the following operation:

detection of conformance to constraints: detecting the error size of a generated preparation model by calculating angular and size constraints of respective sections of the generated preparation, and visually displaying the error distribution condition in a color cloud picture form.

The history-based method is recording both the parametric operations and parameter values according to a model construction sequence to form a model construction tree, and attaching a mark to each operation, wherein when the parameter size is changed, the operation corresponding to the mark is found and a model is reconstructed by this operation with new parameter values according to the construction history so as to complete update of the new model.

A digital control laser automatic tooth preparation device of the present invention includes an intra-oral three-dimensional scanner, a laser, an oral working end of a digital control laser tooth preparation control system, an oral and maxillofacial cone beam CT scanner, a computer, a tooth positioner, a negative-pressure suction device and a real-time monitoring device. The computer is connected respectively with the intra-oral three-dimensional scanner, the dental laser, the oral working end of the digital control laser tooth preparation control system, the oral and maxillofacial cone beam CT scanner, the negative-pressure suction device, and the real-time monitoring device. The laser is connected with the oral working end of the digital control laser tooth preparation control system through a light guiding arm. The oral working end of the digital control laser tooth preparation control system is connected with the tooth positioner and the real-time monitoring device. The negative-pressure suction device is connected with the tooth positioner.

The oral working end of the digital control laser tooth preparation control system includes the light guiding arm, a reflecting mirror cover, a positioner interface, a pedestal, a motor base, a first swing motor, a second swing motor, a double galvanometer system, a linear motor, a focusing lens base, a linear guide, and a grating sensor, wherein the light guiding arm is fixed at a left side of the pedestal; the reflecting mirror cover is located at an end portion of the light guiding arm; the positioner interface is located under the reflecting mirror cover; the linear guide is located on the pedestal; the focusing lens base is located on the linear guide; the grating sensor is located under the focusing lens base; the linear motor is fixed on the pedestal; the first and second swing motors are fixed on the motor base; and the double galvanometer system is connected with the first and second swing motors.

The double galvanometer system includes a first galvanometer, a second galvanometer, a focusing lens, and a reflecting mirror. The first galvanometer is located under the second galvanometer. The focusing lens is located between the second galvanometer and the reflecting mirror. The first galvanometer and the second galvanometer are respectively driven by the first and second swing motors to rotate. The focusing lens is driven by the linear motor.

With the aforementioned technical solutions, the present invention has the following advantages:

The present invention can replace part of manual operations of a doctor, uses a laser to replace a conventional mechanical grinding instrument, can effectively improve the technical level of clinical treatment operations of a primary physician within a short time and improve the efficiency and quality of diagnosis and treatment.

According to another aspect of the present invention, a tooth positioner is provided, which includes a top face and two side faces, wherein when the tooth positioner is mounted in the oral cavity, the top face and the two side faces are respectively corresponding to a top face, a buccal surface and a palatal surface of the tooth in the oral cavity. The top face has a circular opening, the diameter of which is consistent with the inner diameter of a vertical portion of an inlet of the laser working end; the circular opening of the top face is provided at the rear end with a locating component, which is rigidly connected with the vertical portion of the inlet of the laser working end, such that the spatial location relationship of the crown portion of the target tooth, the tooth positioner and the laser working end is fixed; and the front and back lengths of the positioner along the arrangement direction of the teeth can span the target tooth and 1-2 adjacent teeth in front of and behind the target tooth.

According to another aspect of the present invention, a tooth preparation method includes the following steps: 1) acquiring three-dimensional surface scanning data of a crown portion of a target tooth; 2) automatically or manually extracting data of edges of a tooth preparation, and defining design parameters of the tooth preparation, so as to obtain data of the virtual tooth preparation model; 3) obtaining parameters related to a cutting process according to the data of the virtual tooth preparation model acquired in step 2), wherein the parameters related to the cutting process include a focal spot diameter, a spot motion path and a scanning speed of the laser during the tooth preparation; 4) fixing a tooth positioner onto a target tooth and one or more adjacent teeth adjacent to the target tooth, acquiring integrated three-dimensional data of the tooth positioner and the integrated three-dimensional data of the target tooth, registering the data of the virtual preparation model with the integrated three-dimensional data and rigidly connecting an intra-oral working end of the digital control laser tooth preparation control system to an occlusal opening end of the tooth positioner, such that the spatial location relationship of the crown portion of target tooth, the tooth positioner and the intra-oral working end of the digital control laser tooth preparation control system is unified and fixed; and 5) in a coordinate system formed in step 4), performing focusing of the laser at an initial position of the target tooth, controlling a laser spot to complete the tooth preparation process according to the parameters related to the cutting process as set in step 3).

According to another aspect of the present invention, a tooth preparation method includes the following steps: 1) acquiring three-dimensional surface scanning data of a crown portion of a target tooth, and acquiring three-dimensional volume data of the crown portion of the target tooth; 2) registering the two sets of data (i.e., the three-dimensional surface scanning data and the three-dimensional volume data) and unifying the data in the same coordinate system, extracting edges of a tooth preparation, defining design parameters of the tooth preparation, and separating a dental enamel model portion, a dentin model portion and a dental pulp cavity model portion, so as to obtain data of the virtual tooth preparation model; 3) obtaining parameters related to a cutting process according to the data of the virtual tooth preparation model acquired in step 2), wherein the parameters related to the cutting process include a focal spot diameter, a spot motion path and a scanning speed of the laser during the tooth preparation; 4) fixing a tooth positioner onto a target tooth and one or more adjacent teeth adjacent to the target tooth, acquiring integrated three-dimensional data of the tooth positioner and the integrated three-dimensional data of the target tooth, registering the data of the virtual preparation model with the integrated three-dimensional data, and rigidly connecting an intra-oral working end of the digital control laser tooth preparation control system to an occlusal opening end of the tooth positioner, such that the spatial location relationship of the crown portion of target tooth, the tooth positioner and the intra-oral working end of the digital control laser tooth preparation control system is unified and fixed; and 5) in a coordinate formed in step 4), performing focusing of the laser at an initial position of the target tooth, controlling a laser spot to complete the tooth preparation process according to the parameters related to the cutting process as set in step 3).

In the figures: 1. light guiding arm; 2. reflecting mirror cover; 3. positioner interface; 4. focusing lens base; 5. grating sensor; 6. linear guide; 7. linear motor; 8. pedestal; 9. double galvanometer system; 10. first swing motor; 11. second swing motor; 12. motor base; 13. first galvanometer; 14. second galvanometer; 15. focusing lens; 16. reflecting mirror; 17. target tooth; 18. Laser beam; 19 negative-pressure suction device.

DETAILED DESCRIPTION OF THE EMBODIMENTS

The following embodiments are used for illustrating the present invention, instead of limiting the scope thereof.

Figure 1:
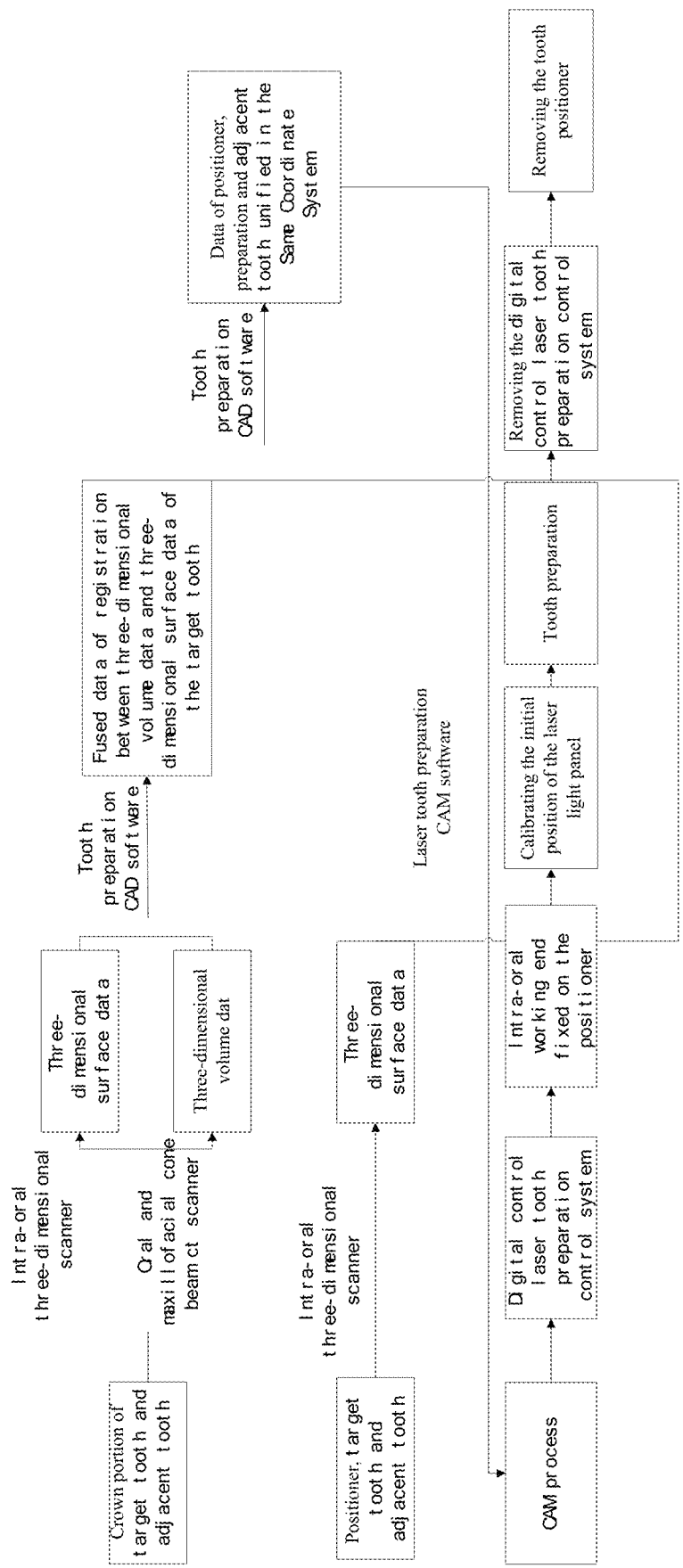
FIG. 1 illustrates a flowchart of an exemplary digital control laser automatic tooth preparation method according to an embodiment of the present invention.

FIG. 1 illustrates a flowchart of an exemplary digital control laser automatic tooth preparation method according to an embodiment of the present invention.

The exemplary digital control laser automatic tooth preparation method includes the following steps:

1) acquiring three-dimensional surface scanning data of a crown portion of a target tooth with an intra-oral three-dimensional scanner, acquiring three-dimensional volume data of the crown portion of the target tooth with an oral and maxillofacial cone beam CT scanner, and storing the two sets of data respectively for subsequent reading operation;

2) registering the two sets of data with tooth preparation CAD software and unifying the data in the same coordinate system, and on the computer screen extracting edges of a tooth preparation, defining design parameters of the tooth preparation, and separating a dental enamel, a dentin and a dental pulp cavity, so as to complete virtual modeling of the tooth preparation, thereby finally storing the results as data of STL format; and 3) automatically generating a focal spot diameter, a spot motion path and a scanning speed of the laser during the tooth preparation, and other parameters related to a cutting process during the tooth preparation with laser tooth preparation CAM software according to the data of the virtual tooth preparation model acquired in step 2), and outputting the parameters into a digital control laser tooth preparation control system, and in an example, the spot motion path includes the cutting path along the direction of Z axis;

the aforementioned laser tooth preparation adopts a layer-by-layer removing method to obtain the preparation, and the entire path planning includes two steps, one is hierarchical cutting and the other is generating a high-efficient laser cutting path for the section contour line obtained from the hierarchical cutting;

the step of fast hierarchical cutting: firstly grouping the triangular patches in the three-dimensional model of the STL-format tooth data into several groups according to different tangent planes intersecting with the triangular patches, wherein the triangular patches of each group all intersect with the same tangent plane; and then intersection computing the triangular patches in each group with a tangent plane, wherein each triangular patch intersects with a tangent plane to obtain an intersected line segment, and according to the continuity of the triangular patches in the three-dimensional model of the STL-format data, an undirected and closed section contour line is formed, without the need of reconstructing a topological structure of a triangular patch or sequencing the resulted intersected line segments;

the step of generating high-efficient laser cutting path of section contour: firstly solving an intersected line segment between a laser cutting region and a filling straight line by using a straight-line filling method and calculating laser cutting lines, then sequencing these cutting lines and performing region dividing to divide a complex cutting region into small and monotonic cutting regions, thereby finally generating a high-efficient laser cutting path;

4) fixing a tooth positioner onto a target tooth and meiso-distal adjacent teeth with a silicon rubber, and removing the silicon rubber around the crown portion of the target tooth, acquiring integrated three-dimensional data of the tooth positioner and the target tooth with the intra-oral three-dimensional scanner again, registering the data of the virtual preparation model with the integrated scanning data by using the software of step 2), and rigidly connecting an intra-oral working end of the digital control laser tooth preparation control system to an occlusal opening end of the tooth positioner through a positioning post located on the tooth positioner, such that the spatial location relationship of the crown portion of target tooth, the tooth positioner and the intra-oral working end of the digital control laser tooth preparation control system is unified and fixed;

5) in a coordinate system formed in step 4), completing accurate focusing of the laser at an initial position of the target tooth by using the laser tooth preparation CAM software, controlling a laser spot to automatically complete the tooth preparation process according to the set scanning path and scanning speed, and meanwhile mounting a negative-pressure suction device on the tooth positioner to remove dental debris in real time;

the working manner of the laser tooth preparation CAM software is as follows:

automatic focusing of the initial position: firstly initializing the position of a lens such that the lens returns back to the initial zero position; then obtaining the coordinate value of the highest point of the target tooth (the largest Z value of the target tooth) from the STL model of the target tooth; and finally calculating the final motion distance of the lens according to the obtained highest tooth coordinate and the parameters of the laser optimal path, such that the focal position of the laser accurately falls at the position of the highest point of the target tooth;

control of automatic tooth preparation process: in the planning of the laser tooth preparation path, performing tooth preparation with a constant speed in a linear cutting manner, wherein each of the laser cutting paths consists of laser cutting line segments of different lengths; in order to achieve laser cutting with constant speed, it needs to perform interpolation processing on the laser cutting line segments, i.e., dividing the laser scanning line segments of different lengths into laser cutting points with small intervals, and converting the three-dimensional coordinate values of the laser cutting points with small intervals into angular displacement of the first and second galvanometers in the laser working head and the linear displacement of the lens through a kinematics inverse operation; since the galvanometers and the lenses are all directly driven, the simultaneous movement of the motor of the first and second galvanometers and the linear motor of the lens can control the laser spot to trace interpolated laser cutting points, thereby achieving laser cutting with constant speed along a planned cutting path and completing the automatic tooth preparation process;

6) completing the tooth preparation, and removing the oral working end of the digital control laser tooth preparation control system and the tooth positioner from the oral cavity of a patient sequentially.

The parameters of the aforementioned cutting process include a scanning speed, a spot diameter, a focus distance, a wavelength, a frequency and a pulse width. There are a great number of combination manners of these parameter values, and it is expected to finally obtain an optimal combination taking multiple respects such as the cutting efficiency, the cutting quality and the temperature control into account.

Through a large number of experiments, the inventor obtained the following combination of parameters related to the cutting process with an excellent performance: a scanning speed of 1700-2100 mm/s, a spot diameter of 25-45 µm, a spot overlapping rate of 0-50%, a wavelength of 780-1064 nm, a repeating frequency of 50-150 KHz, and a pulse width of 25 ps-45 ps. More preferably, through a large number of experiments it is found that the following cutting process parameters have a good performance: a scanning speed of 1900 mm/s (millimeters per second), a spot diameter of 38 µm (micrometers per second), a focal distance of 175 mm (millimeters), a wavelength of 1064 nm (nanometers), a repeating frequency of 100 KHz (kilohertzs), and a pulse width of 15 ps (picoseconds). By setting the laser with such cutting process parameters, the preparation precision of cutting is enhanced by an order of magnitude compared with the clinical requirement, and the cutting speed may be controlled within 17 minutes.

In an example, controlling the laser spot to automatically complete the tooth preparation process according to the set scanning path and scanning speed includes cutting the dental enamel portion and the dentin portion by the hierarchical cutting method. The hierarchical cutting method is a method of hierarchically cutting an object.

A laser working head, as a core component of an automatic laser tooth preparation system, controls a laser focal spot to perform a three-dimensional cutting motion of the laser, i.e., controlling the motion of the laser focal spot on the tooth cross section (the XOY plane) and the motion of the laser focal spot in the tooth depth direction (Z axis).

In the conventional technique, a porcelain tooth is often used for a laser cutting test.

However, the material of the porcelain tooth is significantly different from the material of a human tooth in property. In particular, the porcelain tooth is made of a pure inorganic material, and is sliced outside the human body, without the need of specifically taking problems such as temperature rise related to biosafety into account; while the human tooth is made of an anisotropic and bio-organic material consisting of a dental enamel, a dentin and a enamel-dentinal junction, it theoretically needs to apply different cutting parameters according to different material properties, but the technique for realizing such an application is relatively complex, and the control is more difficult during high-speed scanning and cutting. Due to the collimation of the whole optical path and the influence of differences of different teeth on the experiment results, it needs to work hard for determining preferred cutting parameters.

Through repeat laser cutting experiments on about 500 teeth samples from different sources throughout about 2 years, by researching the inventor of the present invention finds an optimal parameter combination applicable to teeth from different sources and of different tooth hard tissues, and also verifies the precision and effectiveness of the parameters in practical application through experiments.

The inventor finds the following preferred number of cutting layers and the cutting depth per layer as a single stepped size of a hierarchical cutting method: the single stepped size for cutting the dental enamel in the Z axis is 3-7 layers and 30-100 µm, and the single stepped size for cutting the dentin in the Z axis is 3-7 layers and 50-120 µm, wherein the Z axis is the normal vector of the laser focusing plane.

A single stepped size in the Z axis being 3-7 layers and 30-100 μm means that the single stepped size of the laser in the Z axis slices 3-7 layers and the cutting depth per layer is 10-30 μm. A relatively accurate depth error control and an inclination control of a naturally formed side wall can be obtained by using such parameters.

The tooth preparation CAD software may include a data reading module, a preprocessing module, a data fusion module, a constraint modeling module, and a postprocessing module, wherein these modules can perform the following operations when executed by a computing device such as a computer.

The data reading module is configured to perform the following operations:

1) reconstruction of CT data: reading the three-dimensional data reconstructed by a CT image into the tooth preparation CAD software, and performing lighting and rendering;

2) reconstruction of scanning data: reading three-dimensional surface scanning data acquired by scanning the target tooth and three-dimensional volume data acquired by the CT scanner into the software and storing the same for facilitating subsequent reading operations;

the preprocessing module may be configured to perform the following operations:

1) acquisition of curved surface of fusion region: firstly dividing the three-dimensional surface scanning data model acquired by scanning the target tooth into a fusion region and a non-fusion of which the point set is fixed, and clipping and extracting a fusion curved surface from the three-dimensional surface scanning data model by using a finish line extraction algorithm based on a heuristic searching strategy, wherein the heuristic searching strategy is evaluating the cost of each target to be searched to obtain an optimal searching position, and then starting search from this searching position until the final target, so as to remove a large number of meaningless paths and improve the searching efficiency;

2) initial registering based on man-machine interaction: since based on a three-point re-localization theory, three points can build a coordinate relationship, the number of corresponding feature points from the models acquired by the CT scanner and the intra-oral three-dimensional scanner is not less than three, wherein the steps are achieving alignment of the models through alignment of the feature points, calibrating feature points $s_i$ and $s_i'$ respectively on the models acquired by the CT scanner and the intra-oral three-dimensional scanner, calculating a geometric transform matrix R, T between the feature points through $s_i'=s_iR+T$, and applying the matrix to the models acquired by the CT scanner and the intra-oral three-dimensional scanner to perform an initial transformation, wherein this method can significantly reduce a translation error and a rotation error of model registration between subsequent ICP model registrations, and thus provides a good initial value for accurate registration;

3) accurate registration based on ICP algorithm: after the initial registration, performing accurate registration by adopting an ICP algorithm, wherein the position registration between models is rotating and translating the coordinate system of the model acquired by scanning with the intra-oral three-dimensional scanner and the coordinate system of the three-dimensional volume data model acquired by the CT scanner in such a manner that the distance between homologous points is minimum, and making the least square between the spatial changed CT model N and the scanning model M approximate a target function by calculating the optimal rotation matrix $R^k$ and translation vector $T^k$ of the $k^{th}$ iteration, such that the f(R,T) reaches the minimum, as shown in equation (1):

$$f(R, T) = \frac{1}{P}\sum_{i=1}^{P} \|v_i' - (Rv_i + T)\|^2 \to \min \quad (1)$$

wherein, P is the number of the feature points, the data fusion module may be configured to perform the following operations:

1) establishment of differential coordinate: introducing a Laplace operator coefficient matrix L, so as to ensure that the transformation between Cartesian coordinates and differential coordinates is performed in a matrix multiplication manner, as shown in equation (2) below:

$$\Delta = LV, L = I - D^{-1}A \quad (2)$$

wherein $\Delta = \{\delta_i\}$ is a mesh differential coordinate, D is a diagonal matrix, $D_{ii}=d_i$, and A is an adjacency matrix of the mesh;

2) establishment of constraint condition: after the registration between the deformable curved surface of the three-dimensional volume data model N acquired by the CT scanner and the fixed curved surface of the three-dimensional surface scanning data model M acquired by scanning with the intra-oral three-dimensional scanner, realizing extraction of salient-featured points from the three-dimensional surface scanning data model M through a method which combines the mesh saliency and the Morse theory, wherein the constraint condition is in the deformable curved surface of the three-dimensional volume data model N searching closest points corresponding to the feature points extracted from the three-dimensional surface scanning data model M;

3) iteration processing of deformation blending:

during the deformation from the deformable mesh of the three-dimensional volume data model N to the fixed mesh of the three-dimensional surface scanning data model M, employing a multi-iteration deformation strategy, i.e., dividing single deformation into multi-step deformation, wherein this iteration strategy not only makes the deformed mesh be naturally smooth but also avoids a mesh self-intersection phenomenon, and the deformation amount b per time is calculated according to equation (3) below, wherein n is the total number of iteration times, and k is the current number of iteration times:

$$b = \frac{1}{n-k}, k = 0, 1 \ldots n-1 \quad (3)$$

Figure 2:
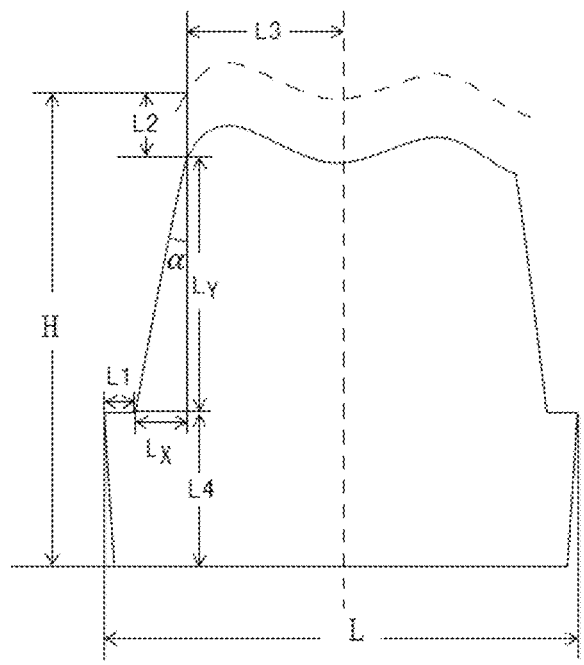
FIG. 2 illustrates a schematic view of constraints of a preparation model according to an embodiment of the present invention.

4) design of deformation weight coefficient: quantifying and assessing the degree of closeness between a deformable point and a target point by designing a weight matrix, wherein the weight matrix is defined by equation (4) below:

$$w_i = w_d(k,d) \times w_a(\alpha) \quad (4)$$

wherein, $w_d(k,d)$ is a distance weighting function, k is the current number of iteration times, i is an index of a feature point, d is a distance between the current deforming point $g_i$ and a target deformation point $v_i$, $w_a(\alpha)$ is an angle weighting function, and $\alpha$ is an included angle between a normal direction of the deforming point $g_i$ and a ray direction $l_i$ from the gravity point of the scanning model to the deforming point; and 5) reconstruction of model mesh: introducing the weight matrix W into a linear equation and an energy function, so as to obtain equations (5) and (6), wherein L is a Laplacian matrix before the target mesh is deformed, I is an m-order unit matrix, L' is a Laplacian matrix after the target mesh is deformed, V' are the vertices after the target mesh is deformed, δ is a Laplacian coordinate of the target mesh, C is the deformation amount of the vertex, $v'_j$ is a coordinate after the deformation of a constraint vertex j, and $c_j$ is a deformation amount of the constraint vertex j;

$$\begin{pmatrix} L \\ wI_{m \times m} \end{pmatrix} V' = L'V' = \begin{pmatrix} \delta \\ wC \end{pmatrix} \quad (5)$$

$$E(V') = \|L'V' - \delta\|^2 + \sum_{j \in C} w\|v'_j - c_j\|^2 \quad (6)$$

the energy function (6) is minimized for solution, and the variable values x',y',z' obtained when the energy function (6) takes the minimum value are used as the expected deformation position of the deformable mesh, wherein precomputation based on Cholesky decomposition is adopted during the solution so as to accelerate the solution;

the constraint modeling module is configured to perform the following operations:

1) extraction of spatial-point-cloud data axes: extracting a dental long axis of a tooth by using an optimum spatial linear fitting method, wherein a directional vector in a space is S=(m,n,p) and a linear equation passing through a point $(x_0, y_0, z_0)$ is as shown in equation (7) below:

$$\frac{x - x_0}{m} = \frac{y - y_0}{n} = \frac{z - z_0}{y} \quad (7)$$

wherein $x_0, y_0, z_0$ is a three-dimensional coordinate value passing through any point, and m,n,p is a coordinate representation of the directional vector, an error equation as shown in equation (8) below is obtained according to a best square approximation theory:

$$f(\varepsilon_{i1}, \varepsilon_{i2}, \varepsilon_{i3}) = \Sigma_{i=0}^{q}(\varepsilon_{i1}^2, \varepsilon_{i2}^2, \varepsilon_{i3}^2) \quad (8)$$

wherein $\varepsilon_{i1}, \varepsilon_{i2}, \varepsilon_{i3}$ are respectively error components of the $i^{th}$ point of the point cloud in directions of the X axis, the Y axis and the Z axis of the fitting straight line, and q is the number of the points;

this non-linear ternary quadratic equation is solved by using an optimum gradient method to obtain an optimum directional vector (m,n,p), and this directional vector can be used with known midpoints to solve a straight line, i.e., the axis of the tooth;

2) spatial curve projection: discretizing a finish line into data point sets by using a dense line projection method, projecting the points onto the three-dimensional volume data model acquired by the CT scanner along a curvature direction point by point, and connecting respective projected points to obtain a projection curve;

3) bias of discrete model: biasing the model by using a point-based bias algorithm, wherein the multiple vectors on the vertices of the mesh are classified depending on types and are endowed with different weight values, and the calculation equation of the bias direction is as shown in equation (9) below:

$$\overline{V}_{Offset} = \sum_{j=1}^{n} W_j \cdot \overline{N}_{i,j} \quad (9)$$

wherein $V_{offset}$ is the bias direction of a point, 1 . . . n is the number of triangular plates surrounding the vertex in a circle, $W_j$ is a weight value varying with the type of the triangular plate, $N_{ij}$ is a normal vector corresponding to respective triangular plates surrounding the vertex in a circle, and the biased model is obtained by biasing respective points in the normal vector direction of each point;

4) analysis and solution of model constraint equation set: setting up a model constraint equation set (10) by analyzing dimensional chain relationships of a constraint model:

$$\begin{cases} \dfrac{L}{2} = L_1 + L_x + L_3 \\ H = L_2 + L_y + L_4 \\ \tan\alpha = \dfrac{L_x}{L_y} \end{cases} \quad (10)$$

wherein, L represents a total buccolingual length; H represents a total longitudinal height of a certain section; $l_1$ and $l_3$ respectively represent a shoulder width and a distance from a surface edge to a long axis of the tooth; $h_1$ and $h_3$ respectively represent a surface preparation thickness and a distance from the finish line to a certain lower designated location; a is the axial wall inclination of the preparation; and $l_2$ and $h_2$ are respectively an edge length and a height corresponding to α, for a complete preparation, n=3 and m=2, wherein $L_1$, $L_2$ and α are three parameterized variable values; for a designated tooth, H, L and $L_4$ are fixed values, and when the parameter values are given, the equation set is the one containing three unknowns, such that a set of values of $L_x$, $L_y$ and $L_3$ can be determined uniquely from the three known equations so as to uniquely determine a preparation model, and thus the spatial positions of respective portions of the model can be determined by solving this constraint equation, as shown in FIG. 2; and 5) parametric modeling of multi-constraint model: driving modeling of a preparation through a parametric operation method, and realizing parametric and dynamic modifications of the model through a history-based method;

the postprocessing module may be configured to perform the following operation:

detection of conformance to constraints: detecting the error size of a generated preparation model by calculating angular and size constraints of respective sections of the generated preparation, and visually displaying the error distribution condition in a color cloud picture form.

The history-based method is recording both the parametric operations and parameter values according to a model construction sequence to form a model construction tree, and attaching a mark to each operation, wherein when the parameter size is changed, the operation corresponding to the mark is found and a model is reconstructed by this operation with new parameter values according to the construction history so as to complete update of the new model.

Figure 3:
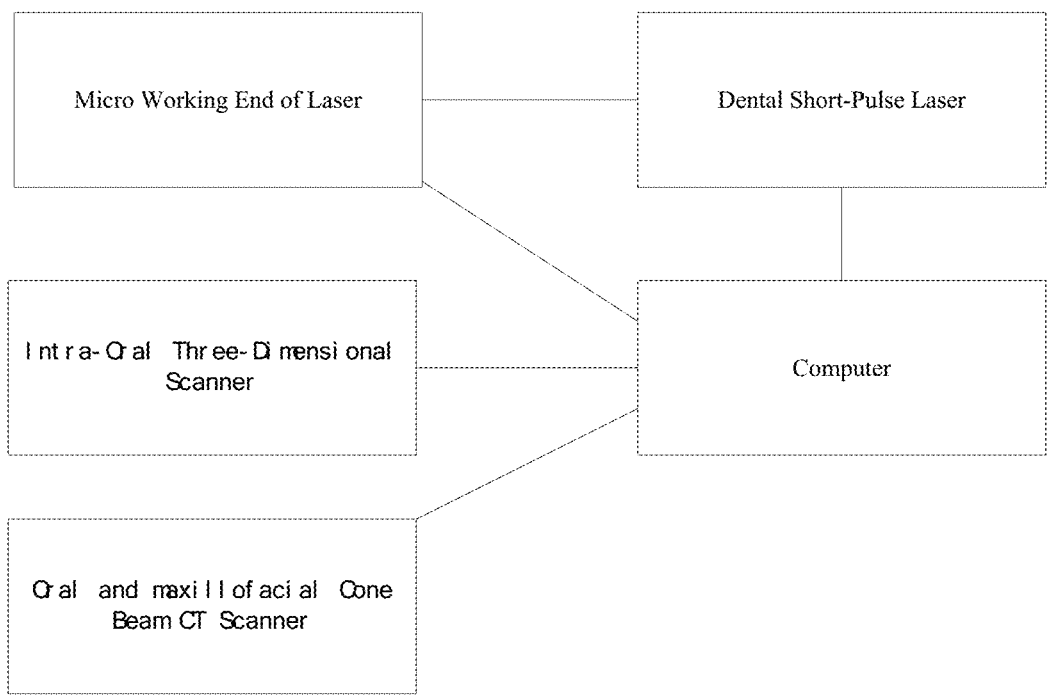
FIG. 3 illustrates a configuration block diagram of an exemplary digital control laser automatic tooth preparation device according to an embodiment of the present invention.

FIG. 3 illustrates a configuration block diagram of an exemplary digital control laser automatic tooth preparation device according to an embodiment of the present invention. The digital control laser automatic tooth preparation device includes an intra-oral three-dimensional scanner, a laser, an oral working end of a digital control laser tooth preparation control system, an oral and maxillofacial cone beam CT scanner, a computer, a tooth positioner, a negative-pressure suction device and a real-time monitoring device. The computer is connected respectively with the intra-oral three-dimensional scanner, the dental laser, the oral working end of the digital control laser tooth preparation control system, the oral and maxillofacial cone beam CT scanner, the negative-pressure suction device, and the real-time monitoring device. The laser is connected with the oral working end of the digital control laser tooth preparation control system through a light guiding arm. The oral working end of the digital control laser tooth preparation control system is connected with the tooth positioner and the real-time monitoring device. The negative-pressure suction device is connected with the tooth positioner.

Figure 4:
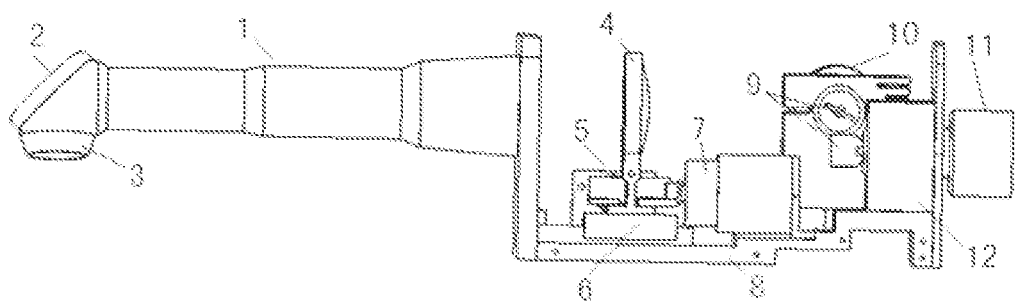
FIG. 4 illustrates a structural schematic view of an oral working end of an exemplary digital control laser tooth preparation control system according to an embodiment of the present invention.
Figure 5:
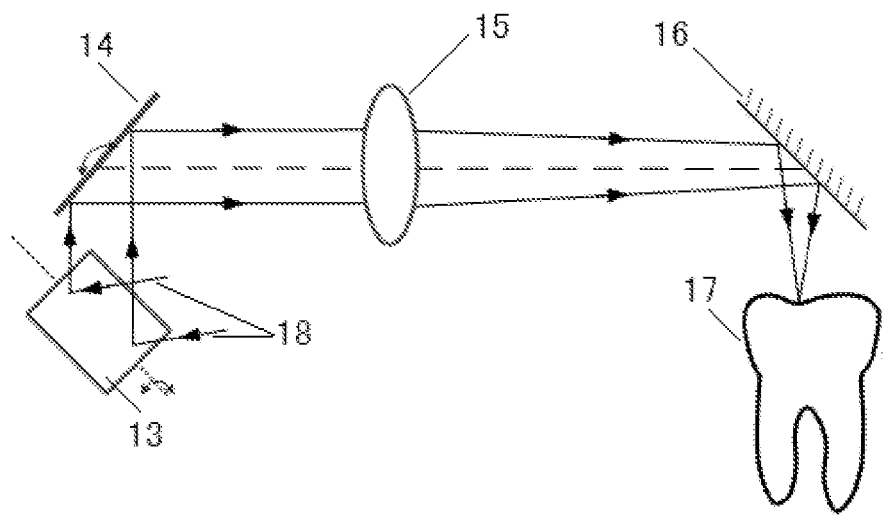
FIG. 5 illustrates a structural schematic view of a double galvanometer system according to an embodiment of the present invention.

FIG. 4 illustrates a structural schematic view of an oral working end of an exemplary digital control laser tooth preparation control system according to an embodiment of the present invention. FIG. 5 illustrates a structural schematic view of a double galvanometer system according to an embodiment of the present invention.

As shown in FIGS. 4 and 5, the oral working end of the exemplary digital control laser tooth preparation control system includes a light guiding arm 1, a reflecting mirror cover 2, a positioned interface 3, a focusing lens base 4, a motor base 12, a first swing motor 10, a second swing motor 11, double galvanometer systems 13 and 14, a linear motor 7, a focusing lens base 4, a linear guide 6, and a grating sensor 5. The light guiding arm 1 is fixed at the left side of a pedestal 8. The reflecting mirror cover is located at an end portion of the light guiding arm 1. The positioner interface is located under the reflector cover. The linear guide 6 is located on the pedestal 8. The focusing lens base 4 is located on the linear guide 6. The grating sensor 5 is located under the focusing lens base 4. The linear motor 7 is fixed on the pedestal 8. The first swing motor 10 and the second swing motor 11 are fixed on the motor base. The double galvanometer systems 13 and 14 are connected with the first swing motor 10 and the second swing motor 11.

As shown in FIG. 5, the double galvanometer system includes a first galvanometer 13, a second galvanometer 14, a focusing lens 15, and a reflecting mirror. The first galvanometer 13 is located under the second galvanometer 14. The focusing lens 15 is located between the second galvanometer 14 and the reflecting mirror. The first galvanometer 13 and the second galvanometer 14 are respectively driven by the first swing motor 11 and the second swing motor 12 to rotate. The focusing lens 15 is driven by the linear motor 7.

Figures 6A, 6B:
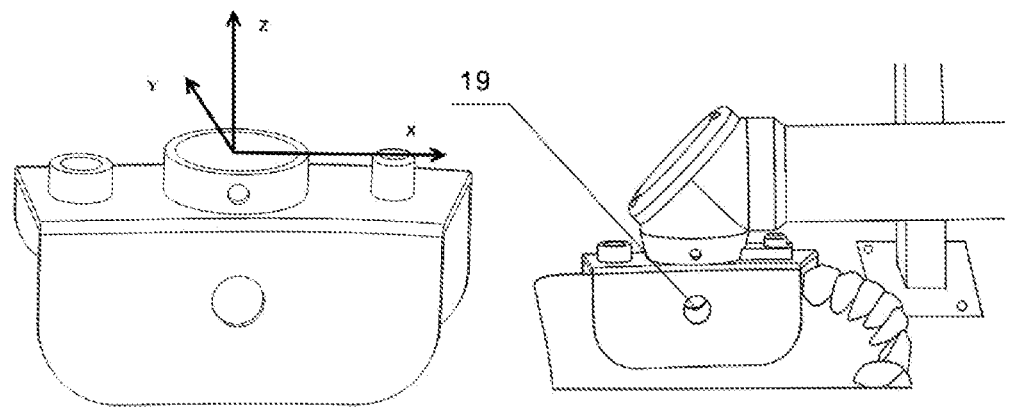
FIG. 6A and FIG. 6B respectively illustrate a perspective schematic view and a schematic working status view of a tooth positioner according to an embodiment of the present invention.

FIG. 6A and FIG. 6B respectively illustrate a perspective schematic view (the left figure) and a schematic working status view (the right figure) of a tooth positioner according to an embodiment of the present invention.

The tooth positioner includes a top face and two side faces, wherein when the tooth positioner is mounted in the oral cavity, the top face and the two side faces are respectively corresponding to a top face, a buccal surface and a palatal surface of the tooth in the oral cavity. The top face has a circular opening, the diameter of which is consistent with the inner diameter of a vertical portion of an inlet of the laser working end; the circular opening of the top face is provided at the rear end with a locating component, which is rigidly connected with the vertical portion of the inlet of the laser working end, such that the spatial location relationship of the crown portion of the target tooth, the tooth positioner and the laser working end is fixed; and the front and back lengths of the positioner along the arrangement direction of the teeth can span the target tooth and 1-2 adjacent teeth in front of and behind the target tooth.

The tooth positioner enables a tight fixation of teeth, can be connected with a laser working head seamlessly so as to realize a high-precision tooth preparation operation of the target tooth, and provides a coordinate system for the geometric tooth model obtained by using the intra-oral scanner, so as to ensure that the geometric data of the target tooth is consistent with the coordinate system of the laser working head.

In an example, each of the top face and two side faces of the tooth positioner has a porous structure to facilitate the fixation of the tooth positioner onto the surfaces of the adjacent tooth and the peripheral soft tissue with the silicon rubber, and the silicon rubber protects the adjacent tooth and the peripheral soft tissue from harms.

In an example, at least one of the two side faces has one or more openings, wherein one of the openings is connected with an external cooling device such as an air cooling means. In an example, at least one of the two side faces has one or more openings, wherein one of the openings is connected with a negative-pressure suction device for removing debris generated in the tooth cutting process.

In an example, the radian of the two side faces of the tooth positioner is consistent with that of the dental arch of the fixed tooth.

In an example, the inner surfaces of the three faces of the tooth positioner are spaced apart from the surfaces of the target tooth, the meiso-distal adjacent teeth and the peripheral alveolar bone with a gap, so as to accommodate the silicon rubber material for fixing. In an example, the gap is 0.5-2 mm. Particularly, the gap may be 1 mm.

In an example, an induction port is arranged on the tooth positioner to sense whether the laser is in a safe region, thereby protecting the tongue and oral parts of a patient from hurts.

In an example, each of the three faces of the tooth positioner has three circular openings at the central position thereof, wherein the diameter of the opening is 15 mm, which is greater than or equal to the maximum diameter of the cross sections of all teeth in the oral cavity and is consistent with the inner diameter of the vertical portion of the inlet of the laser working end.

In an example, a locating pin is arranged at the rear end of the circular opening of the top face, and is engaged with the vertical portion of the inlet of the laser working end, so as to play a role in locating and fixing.

In an example, an endoscope is mounted on the tooth positioner so as to observe the ambient environment of the tooth.

Figure 7:
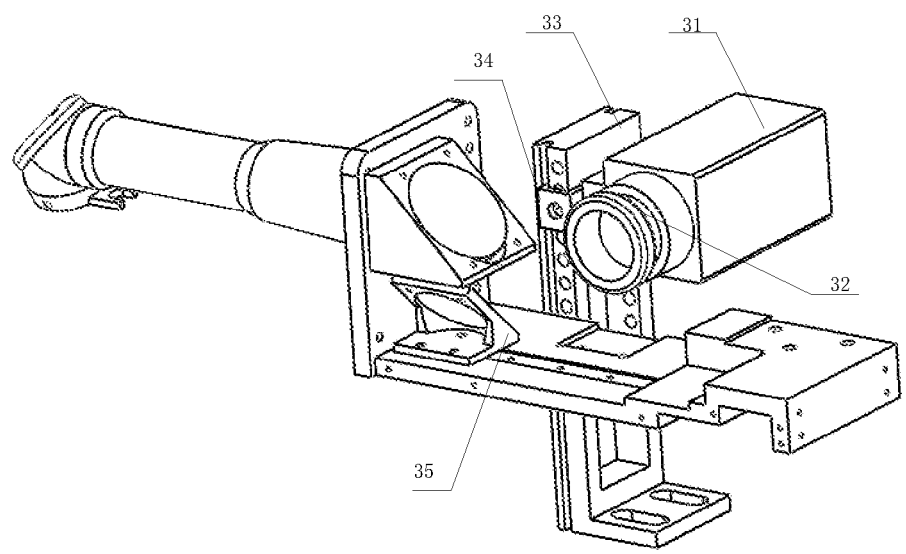
FIG. 7 illustrates a structural schematic view of a real-time monitoring device according to an embodiment of the present invention.
Figure 8:
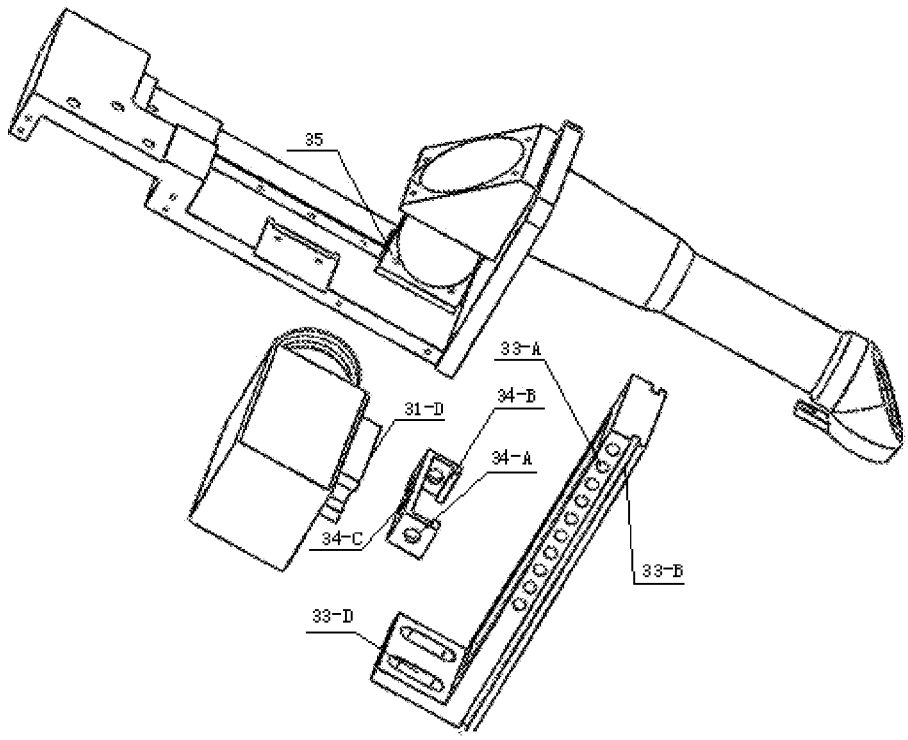
FIG. 8 illustrates another structural schematic view of a real-time monitoring device according to an embodiment of the present invention.

An exemplary structure of the real-time monitoring device according to an embodiment of the present invention is described hereafter with reference to FIGS. 7 and 8.

FIG. 7 illustrates a structural schematic view of a real-time monitoring device according to an embodiment of the present invention.

FIG. 8 illustrates another structural schematic view.

With reference to FIGS. 7 and 8, in the monitoring assembly, an industrial lens 32 is connected to a CCD image sensor 31 through a thread; a surface 31-D of the CCD image sensor 31 is fixed on a surface 34-C of a CCD camera connector 34 through a bolt; a surface 34-B of the CCD camera connector 34 can slide freely up and down in a groove 33-B of a CCD camera supporter 33; a hole 34-A of the CCD camera connector 34 and a hole 33-B of the CCD camera supporter 33 are fixed together through a bolt; the aforementioned CCD camera supporter can be fixed on a large operation desk through a hole 33-D thereof; and the center of the CCD image sensor 31 is in the same horizontal line with the center of a reflecting mirror (not shown) mounted on a reflecting-minor mounting base 35.

According to an embodiment of the present invention, a tooth preparation method is provided, which includes the following steps:

1) acquiring three-dimensional surface scanning data of a crown portion of a target tooth;

2) automatically or manually extracting data of preparation edges, and defining design parameters of the tooth preparation, so as to obtain data of a virtual tooth preparation model;

3) obtaining parameters related to a cutting process according to the data of the virtual tooth preparation model acquired in step 2), wherein the parameters related to the cutting process include a focal spot diameter, a spot motion path and a scanning speed of the laser during the tooth preparation;

4) fixing a tooth positioner onto a target tooth and one or more adjacent teeth adjacent to the target tooth, acquiring integrated three-dimensional data of the tooth positioner and the integrated three-dimensional data of the target tooth, registering the data of the virtual preparation model with the integrated three-dimensional data, and rigidly connecting an intra-oral working end of the digital control laser tooth preparation control system to an occlusal opening end of the tooth positioner, such that the spatial location relationship of the crown portion of the target tooth, the tooth positioner and the intra-oral working end of the digital control laser tooth preparation control system is unified and fixed; and 5) in a coordinate system formed in step 4), performing focusing of the laser at an initial position of the target tooth, controlling a laser spot to complete the tooth preparation process according to the parameters related to the cutting process as set in step 3).

According to another embodiment of the present invention, a tooth preparation method is provided, which includes the following steps:

1) acquiring three-dimensional surface scanning data of a crown portion of a target tooth, and acquiring three-dimensional volume data of the crown portion of the target tooth;

2) registering the two sets of data (i.e., the three-dimensional surface scanning data and the three-dimensional volume data) and unifying the data in the same coordinate system, extracting edges of a tooth preparation, defining design parameters of the tooth preparation, and separating a dental enamel model portion, a dentin model portion and a dental pulp cavity model portion, so as to obtain data of the virtual tooth preparation model, wherein the extraction of the edges of the tooth preparation can be conducted manually on a computer screen or conducted automatically through software programming;

3) obtaining parameters related to a cutting process according to the data of the virtual tooth preparation model acquired in step 2), wherein the parameters related to the cutting process include a focal spot diameter, a spot motion path and a scanning speed of the laser during the tooth preparation;

4) fixing a tooth positioner onto a target tooth and one or more adjacent teeth adjacent to the target tooth, acquiring integrated three-dimensional data of the tooth positioner and the integrated three-dimensional data of the target tooth, registering the data of the virtual preparation model with the integrated three-dimensional data, and rigidly connecting an intra-oral working end of the digital control laser tooth preparation control system to an occlusal opening end of the tooth positioner, such that the spatial location relationship of the crown portion of target tooth, the tooth positioner and the intra-oral working end of the digital control laser tooth preparation control system is unified and fixed; and 5) in a coordinate system formed in step 4), performing focusing of the laser at an initial position of the target tooth, controlling a laser spot to complete the tooth preparation process according to the parameters related to the cutting process as set in step 3).

In an example, the parameters related to the cutting process include: a scanning speed of 1900 mm/s (millimeters per second), a spot diameter of 38 μm (micrometers per second), a focal distance of 175 mm (millimeters), a wavelength of 1064 nm (nanometers), a repeating frequency of 100 KHz (kilohertzs), and a pulse width of 15 ps (picoseconds). In an example, the step of controlling the laser spot to automatically complete the tooth preparation process according to the scanning path and scanning speed as set in step 3) includes cutting the dental enamel portion and the dentin portion by the hierarchical cutting method.

In an example, the single stepped size in the Z axis for cutting the dental enamel is 3-7 layers and 30-70 μm, and the single stepped size in the Z axis for cutting the dentin is 3-7 layers and 25-75 μm, wherein the Z axis is an axis in a direction perpendicular to the tooth.

Figure 9:
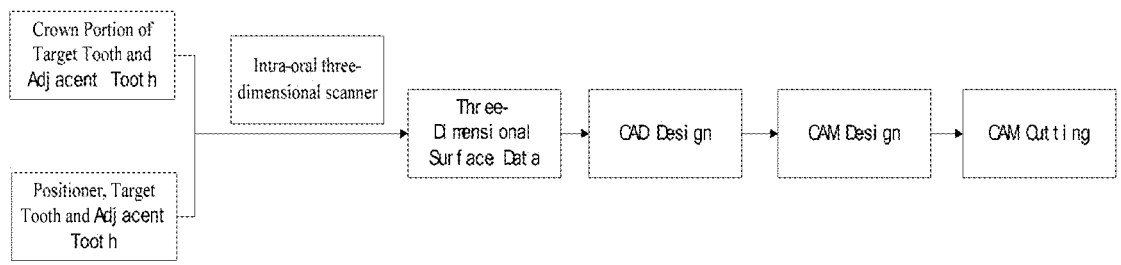
FIG. 9 illustrates a flowchart of an exemplary digital control laser automatic tooth preparation method according to another embodiment of the present invention.

FIG. 9 illustrates a schematic flowchart of an exemplary digital control laser automatic tooth preparation method according to another embodiment of the present invention.

The digital control laser automatic tooth preparation method as shown in FIG. 9 mainly differs from the method as shown in FIG. 1 in that, it only needs to use the intra-oral three-dimensional scanner to acquire the three-dimensional surface scanning data of the crown portion of the target tooth, without using the oral and maxillofacial cone beam CT scanner to acquire the three-dimensional volume data of the crown portion of the target tooth. Subsequently, computer aided design (CAD), computer aided manufacturing (CAM) design and CAM cutting are performed based on so acquired three-dimensional surface scanning data. The realization of respective steps as shown in FIG. 9 may be the same as that of the corresponding steps described previously in conjunction with FIG. 1, except removal of the step of acquiring the three-dimensional volume data of the crown portion of the target tooth and operations related to the three-dimensional volume data.

Obviously, the aforementioned embodiments of the present invention are merely examples used for clearly illustrating the present invention, rather than limiting the implementation of the present invention. As will be understood by those of ordinary skills in the art, other changes or modifications of different forms can be made based on the aforementioned illustration. Herein, the embodiments are not exhaustive. Apparent changes or modifications derived from the technical solutions of the present invention still fall into the protection scope of the present invention.

What is claimed is:

1. A digital control laser automatic tooth preparation device, comprising an intra-oral three-dimensional scanner, a laser, an oral working end, an oral and maxillofacial cone beam CT scanner, a computer, a tooth positioner, a negative-pressure suction device and a real-time monitoring device, wherein the computer is connected respectively with the intra-oral three-dimensional scanner, the laser, the oral working end, the oral and maxillofacial cone beam CT scanner, the negative-pressure suction device, and the real-time monitoring device; the oral working end is connected with the tooth positioner and the real-time monitoring device; and the negative-pressure suction device is connected with the tooth positioner, the intra-oral three-dimensional scanner acquires three-dimensional surface scanning data of a crown portion of a target tooth, the oral and maxillofacial cone beam CT scanner acquires three-dimensional volume data of the crown portion of the target tooth, the computer registers the three-dimensional surface scanning data and the three-dimensional volume data with a tooth preparation CAD software and unifies the three-dimensional surface scanning data and the three-dimensional volume data in a same coordinate system, and on a computer screen automatically or manually extracts edges of a tooth preparation, defines design parameters of the tooth preparation, and separates a dental enamel model portion, a dentin model portion and a dental pulp cavity model portion, so as to complete virtual modeling of the tooth preparation and obtain data of a virtual tooth preparation model;

the computer automatically generates parameters related to a cutting process according to the data of the virtual tooth preparation model, wherein the parameters related to the cutting process comprise a focal spot diameter, a spot motion path and a scanning speed of the laser during tooth preparation, the laser is optically connected with the oral working end, the oral working end is configured to control the parameters relating to the cutting process and comprises a cover, a positioner interface, a pedestal, a first swing motor, a second swing motor, a base for the first and second swing motors, a double galvanometer system, a linear motor, a focusing lens, a base for the focusing lens, a linear guide, and a grating sensor, a light guiding arm, wherein the light guiding arm is fixed at a left side of the pedestal; the cover is located at an end portion of the light guiding arm; the positioner interface is located under the cover; the linear guide is located on the pedestal; the base for the focusing lens is located on the linear guide; the grating sensor is located under the base for the focusing lens; the linear motor is fixed on the pedestal, the first and second swing motors are fixed on the base for the first and second swing motors; and the double galvanometer system is connected with the first and second swing motors, the linear motor is located between the focusing lens and the swing motors.

2. The digital control laser automatic tooth preparation device of claim 1, wherein the double galvanometer system comprises a first galvanometer, a second galvanometer, the focusing lens and a reflecting mirror; wherein the reflecting mirror is configured to direct light from the focusing lens onto the target tooth; wherein the first galvanometer is located under the second galvanometer; the focusing lens is located between the second galvanometer and the reflecting mirror; the first galvanometer and the second galvanometer are respectively driven by the first and second swing motors to rotate; and the focusing lens is driven by the linear motor.

3. The digital control laser automatic tooth preparation device of claim 1, wherein the tooth positioner comprises a top face and two side faces, wherein when the tooth positioner is mounted in an oral cavity, the top face and the two side faces are respectively corresponding to an occlusal surface, a buccal surface and a palatal surface of the target tooth in the oral cavity, the top face has a circular opening, a diameter of which is consistent with an inner diameter of the positioner interface.

* * * * *